(12) United States Patent
Orlu

(10) Patent No.: US 10,898,117 B2
(45) Date of Patent: Jan. 26, 2021

(54) SAFETY CONNECTOR WITH NEEDLE

(71) Applicant: P2A MEDICAL, Maxilly sur Leman (FR)

(72) Inventor: Alain Orlu, Viuz la Chiesaz (FR)

(73) Assignee: P2A MEDICAL, Maxilly sur Leman (FR)

( * ) Notice: Subject to any disclaimer, the term of this patent is extended or adjusted under 35 U.S.C. 154(b) by 669 days.

(21) Appl. No.: 15/560,540

(22) PCT Filed: Mar. 25, 2016

(86) PCT No.: PCT/IB2016/051707
§ 371 (c)(1),
(2) Date: Sep. 22, 2017

(87) PCT Pub. No.: WO2016/151540
PCT Pub. Date: Sep. 29, 2016

(65) Prior Publication Data
US 2018/0110453 A1 Apr. 26, 2018

(30) Foreign Application Priority Data

Mar. 25, 2015 (FR) .................................... 15 52473

(51) Int. Cl.
*A61B 5/15* (2006.01)
*A61J 1/20* (2006.01)
*A61B 5/154* (2006.01)
*A61B 5/153* (2006.01)
(Continued)

(52) U.S. Cl.
CPC ...... *A61B 5/150641* (2013.01); *A61B 5/1438* (2013.01); *A61B 5/15003* (2013.01); *A61B 5/153* (2013.01); *A61B 5/154* (2013.01); *A61B 5/150236* (2013.01); *A61B 5/150274* (2013.01); *A61B 5/150389* (2013.01); *A61B 5/150503* (2013.01); *A61B 5/150572* (2013.01); *A61B 5/150732* (2013.01); *B29C 45/14336* (2013.01);
(Continued)

(58) Field of Classification Search
CPC .......... A61J 1/20–2096; A61B 5/1438; A61B 5/15003; A61B 5/150236; A61B 5/150274; A61B 5/150389; A61B 5/150503; A61B 5/150572; A61B 5/150641; A61B 5/150732; A61B 5/153; A61B 5/154

See application file for complete search history.

(56) References Cited

U.S. PATENT DOCUMENTS

2011/0264037 A1\* 10/2011 Foshee .................. A61J 1/2096
604/88

FOREIGN PATENT DOCUMENTS

| EP | 1557124 A1 | 7/2005 | |
|---|---|---|---|
| EP | 2070476 A1 \* | 6/2009 | ........... A61B 5/1405 |
| EP | 2070476 A1 | 6/2009 | |

(Continued)

*Primary Examiner* — Benjamin J Klein
(74) *Attorney, Agent, or Firm* — William H. Eilberg

(57) ABSTRACT

A safety connector has a needle, and includes a tubular protective sleeve with a distal section, having a movable wall portion arranged in the peripheral wall thereof. The movable wall portion is selectively movable between a retracted position and a protection position. In the retracted position, the movable wall portion is aligned with the peripheral wall of the proximal section of the tubular protective sleeve. In the protection position, the movable wall portion projects into the inner space of the tubular protective sleeve.

17 Claims, 11 Drawing Sheets

(51) Int. Cl.
 B29C 45/14 (2006.01)
 B29L 31/00 (2006.01)
(52) U.S. Cl.
 CPC . B29C 45/14598 (2013.01); *B29L 2031/7544* (2013.01)

(56) References Cited

FOREIGN PATENT DOCUMENTS

| | | | | |
|---|---|---|---|---|
| EP | 2090278 A1 | * | 8/2009 | ............ A61J 1/2089 |
| JP | H3 111307 U | | 11/1991 | |
| JP | H11 290298 A | | 10/1999 | |

* cited by examiner

SAFETY CONNECTOR WITH NEEDLE

TECHNICAL FIELD OF THE INVENTION

The present invention relates to safety connectors for connecting a sampling container to a fluid-carrying channel. The invention relates in particular to such a connector for taking blood samples in applications in the health sector.

When taking blood samples, in particular for blood donations, the blood must be systematically analyzed by collecting a small quantity of blood in a sampling container. To this end, a fluid-carrying channel must be connected removably and in a leaktight manner to a sampling container under conditions of absolute hygiene, necessitating minimum movement of the operator for connecting the sampling container to the channel and for disconnecting it therefrom.

At the same time, the operator has to be protected against all risks of injury and contamination by the blood sample.

To this end, there has already been designed a safety connector with needle, such as described in the document. EP 1 557 124, comprising a hollow needle for passage of fluid, a needle support sleeve, and a protective tubular sleeve extending along a longitudinal axis, the needle support sleeve carrying the needle and connecting it in a leaktight manner to a fluid-carrying channel to which it is fixed, a protruding needle portion axially continuing the needle support sleeve at the end opposite the fluid-carrying channel, the tubular protective sleeve having an inner space containing the protruding needle portion, with an open distal end for the introduction of a sampling container to be connected by the needle, and with a proximal end through which the needle support sleeve passes. The tubular protective sleeve has a proximal segment developing from its closed proximal end in line with the protruding needle portion, and has a distal segment continuing the proximal segment between the protruding needle portion and the distal end of the tubular protective sleeve.

The needle is thus contained in the tubular protective sleeve at a distance from the open distal end, which limits the risk of the operator being pricked by the needle. To further improve the safety of the operator, the connector of the document EP 1 557 124 has a seal that can be folded over to close the open distal end of the tubular protective sleeve. In the closure position, the fold-over seal prevents the user from inserting a finger into the tubular protective sleeve in the direction of the sharp end of the needle.

The disadvantage of the connector of EP 1 557 124 is that the production of the fold-over seal significantly increases the manufacturing costs, if only through the amount of additional material intended to form the fold-over seal.

Moreover, the fold-over seal may accidentally open during the manipulation or transport of the container, with the result that it may be open when the operator grasps the connector. There is then a risk of the operator inadvertently placing one of his fingers in the protective sleeve and being pricked by the needle.

The earlier document JP H3-11307 U, which is also cited by the earlier document JP H11-290298 A, describes a safety connector with needle, of which the fluid-carrying channel is in the form of a needle intended to penetrate a vein of the patient. This needle is in fact a double needle, the other end of which protrudes into the inner space of a tubular protective sleeve with an open distal end for the insertion of a sampling container to be connected by the needle. A protective sheath surrounds the protruding needle part in the tubular protective sleeve. The rolling up of this sheath may cause an elastic compression thereof, and the sheath may sometimes tend to recover its shape by ejecting the sampling container. To avoid such ejection, the document JP H3-111307 U describes an oblong locking ring which is elastically deformable and which is engaged in two diametrically opposite lateral openings of the tubular protective sleeve. This ring is not designed to oppose the insertion of a user's finger; on the contrary, it is intended to easily deform in order to allow the passage of a sampling container that is introduced into the tubular protective sleeve. This ring is produced separately from the tubular protective sleeve, which makes the manufacturing process more complex and more costly. This locking ring may also be accidentally lost. Moreover, probably with a view to limiting the risk of accidental loss, a functional clearance is provided such that the locking ring permanently protrudes at least partially into the inner space, even during the passage of the sampling container stopper in the elastic ring when a sampling container is introduced into the tubular protective sleeve.

DISCLOSURE OF THE INVENTION

A problem addressed by the present invention is that of designing a safety connector with needle which effectively limits the risks of the operator being accidentally pricked.

At the same time, the invention has the aim of ensuring effective protection of the operator, before and after sampling, at less cost.

In order to achieve these objects and others, the invention proposes a safety connector with needle, comprising a hollow needle for passage of fluid, a needle support sleeve, and a tubular protective sleeve extending along a longitudinal axis, the needle being connected in a leaktight manner to a fluid-carrying channel to which the needle support sleeve is fixed, a protruding needle portion axially continuing the needle support sleeve at the end opposite the fluid-carrying channel, the tubular protective sleeve having an inner space defined by a peripheral sleeve wall and containing the protruding needle portion, with an open distal end for the introduction of a sampling container to be connected by the needle, and with a proximal end through which the needle support sleeve passes, the tubular protective sleeve having a proximal segment with a proximal peripheral wall developing from its proximal end in line with the protruding needle portion, and having a distal segment with a distal peripheral wall continuing the proximal segment between the protruding needle portion and the distal end of the tubular protective sleeve;
according to the invention:
  the distal peripheral wall has at least one wall portion selectively movable between a retracted position and a protection position,
  in the retracted position, the movable wall portion does not protrude into the inner space,
  in the protection position, the movable wall portion projects into the inner space in order to form an obstacle that at least partially blocks the inner space in the distal segment.

Since the movable wall portion is formed in the peripheral lateral wall of the distal segment, its production does not require addition of any more material than is necessary for the production of the tubular protective sleeve. The obstacle, which the movable wall portion can form in order to at least partially block the inner space in the distal segment, is formed in one piece with the distal peripheral wall. This obstacle is thus produced economically, without the need to add more material than is necessary for the production of the tubular protective sleeve, and in any case cannot be accidentally lost.

When the connector is supplied to the operator, the movable wall portion may already be arranged in the projecting position in such a way as to prevent one of the operator's fingers from penetrating the tubular protective sleeve as far as the needle.

Before introducing a sampling tube, the operator moves the movable wall portion to the retracted position. The movable wall portion no longer protrudes into the inner space of the tubular protective sleeve, and the latter is then able to receive a sampling tube.

After withdrawing the sampling tube at the end of the sampling procedure, the operator moves the movable wall portion to the projecting position. The movable wall portion then once again partially blocks the open distal end of the tubular protective sleeve, in order to avoid a finger of an operator being able to penetrate the tubular protective sleeve and being pricked on the needle.

In order to better reduce the risk of an operator pricking his finger, provision is made that, in the protection position, the movable wall portion can be at least partially situated in the vicinity of the longitudinal axis, in a continuation of the protruding needle portion in the inner space of the tubular protective sleeve. In the projecting position, the movable wall portion is thus arranged, along the longitudinal axis and perpendicularly with respect to the longitudinal axis, at least partially between the end of the needle and the open distal end of the protective sleeve. Whatever the diameter of the operator's finger, the latter then necessarily comes into contact with the movable wall portion, which prevents said finger from being pricked on the needle.

In a particular embodiment of the invention, provision can be made that:
the movable wall portion has first and second flaps formed in the distal peripheral wall,
the first and second flaps are respectively articulated on the rest of the distal peripheral wall in a first hinge zone and a second hinge zone, respectively permitting a pivoting of the first and second flaps about a first pivot axis and a second pivot axis parallel to the longitudinal axis,
the first and second flaps are articulated on each other in a third hinge zone, permitting a relative pivoting of the first and second flaps with respect to each other about a third pivot axis parallel to the longitudinal axis,
the first and second flaps are movable by pivoting, about first and second pivot axes, between a retracted position and a protection position,
in the retracted position, the first and second flaps are aligned with the peripheral wall of the proximal segment of the tubular protective sleeve,
in the protection position, the first and second flaps project into the inner space of the tubular protective sleeve.

Such flaps are easy to produce and are easy for an operator to manipulate.

On account of the pivot axes being oriented parallel to the longitudinal axis, the movement of the movable wall portion is necessarily perpendicular to the longitudinal axis. As a result, an axial force applied to the movable wall portion by a user's finger does not risk causing the movable wall portion to retract and the finger to penetrate as far as the needle.

Advantageously, the first, second and third hinge zones can be produced by a local thinning of the material thickness of the peripheral sleeve wall. Such thinning can be easily obtained, without a tool change, during the injection of the tubular protective sleeve when the latter is made of plastic. Good results have been achieved with a tubular protective sleeve made of polypropylene or of polyacetal.

Provision can preferably be made that:
the tubular protective sleeve has a circular cross section,
the first and second pivot axes are separated from each other by an angle sector of less than 180°.

It is thus certain that, when the first and second flaps are in the projecting position, they are in a position of stable equilibrium. This means that, starting from their projecting position, the flaps first have to be pivoted by a certain angular extent (by application of an external force), from their projecting position to their retracted position, before they can move by themselves to the retracted position (in the absence of an external force). This reduces the risk of the first and second flaps accidentally returning to the retracted position under the effect of a jolt or vibrations during transport or handling.

Results providing satisfactory protection have been obtained with first and second pivot axes separated from each other by an angle sector of between about 120° and about 170°.

Advantageously, the movable wall portion can extend, along the longitudinal axis, by a distance of between about 12 mm and about 15 mm.

Such a movable wall portion has a height sufficient for it to be easily driven by an operator's finger into the inner space of the tubular protective sleeve, from its retracted position to its projecting position.

Provision can preferably be made that:
the safety connector with needle has pushing means which are formed in the distal peripheral wall and/or in the proximal peripheral wall and are situated at least partially in line with the movable wall portion,
the pushing means are at least partially movable transversely between a rest position and at least one pushing position, being returned elastically to their rest position,
in the rest position, the pushing means do not protrude into the inner space and are preferably aligned with the proximal peripheral wall,
in the pushing position, the pushing means project into the inner space of the tubular protective sleeve in order to stress the movable wall portion and return it to the retracted position.

Such pushing means allow the operator to move the movable wall portion from its projecting position to its retracted position without having to introduce a finger into the open distal end of the tubular protective sleeve. To move the movable wall portion from its projecting position to its retracted position, it suffices for the operator to radially press the lateral part in which the pushing means are formed. Beneath the operator's fingers there is always a material thickness (equal to the material thickness of the tubular protective sleeve) such that the risk of the operator pricking his fingers during the manipulation of the pushing means is low.

Since the pushing means are formed in the peripheral lateral wall of the tubular protective sleeve, their manufacture does not require any additional material compared to a tubular protective sleeve of the prior art.

Provision can preferably be made that:
the pushing means are in the form of a tongue extending along the longitudinal axis between a first end and a free second end,
the tongue is articulated at its first end on the rest of the proximal peripheral wall and/or of the distal peripheral wall in a fourth hinge zone, permitting a pivoting of the tongue about a fourth pivot axis perpendicular to the longitudinal axis, the free second end of the tongue is situated in line with the movable wall portion.

Advantageously, the free second end of the tongue can have a pushing zone which extends, along the longitudinal axis, by a distance of between about 12 mm and about 15 mm and extends, perpendicularly with respect to the longitudinal axis, by a distance of between about 10 mm and about 18 mm.

The free end of the tongue thus has dimensions sufficient for it to be easily driven by an operator's finger into the inner space of the tubular protective sleeve, from the rest position to the pushing position.

To ensure a good level of efficacy in their use for moving the movable wall portion from its projecting position to is retracted position, the pushing means can be situated diametrically opposite the movable wall portion in relation to the longitudinal axis.

Provision can preferably be made that:
the tubular protective sleeve has, at its open distal end, a radial widening,
the movable wall portion is formed, along the longitudinal axis, in immediate proximity to the open distal end.

The radial widening constitutes an annular rib for stiffening the tubular protective sleeve. The open distal end of the tubular protective sleeve thus better retains the shape of its cross section to allow a sampling tube to be engaged therein. This also contributes to keeping the movable wall portion in a stable projecting position.

Advantageously, the tubular protective sleeve can be overmolded on the needle support sleeve. The join obtained by overmolding between the tubular protective sleeve and the needle support sleeve ensures good leaktightness of the tubular protective sleeve in the vicinity of its proximal end. This allows any drops of blood to be retained in the tubular protective sleeve.

According to another aspect of the invention, a method is proposed for producing a safety connector with needle of the kind described above. According to the invention, this production method comprises a step of plastic injection molding, during which the tubular protective sleeve is formed in one go and provided with:
cutouts, and if appropriate a reduced material thickness, forming the movable wall portion,
if appropriate, cutouts forming the pushing means.

BRIEF DESCRIPTION OF THE DRAWINGS

Other objects, features and advantages of the present invention will become clear from the following description of particular embodiments, said description being given with reference to the appended drawings, in which.

DESCRIPTION OF THE PREFERRED EMBODIMENTS

Figure 1:
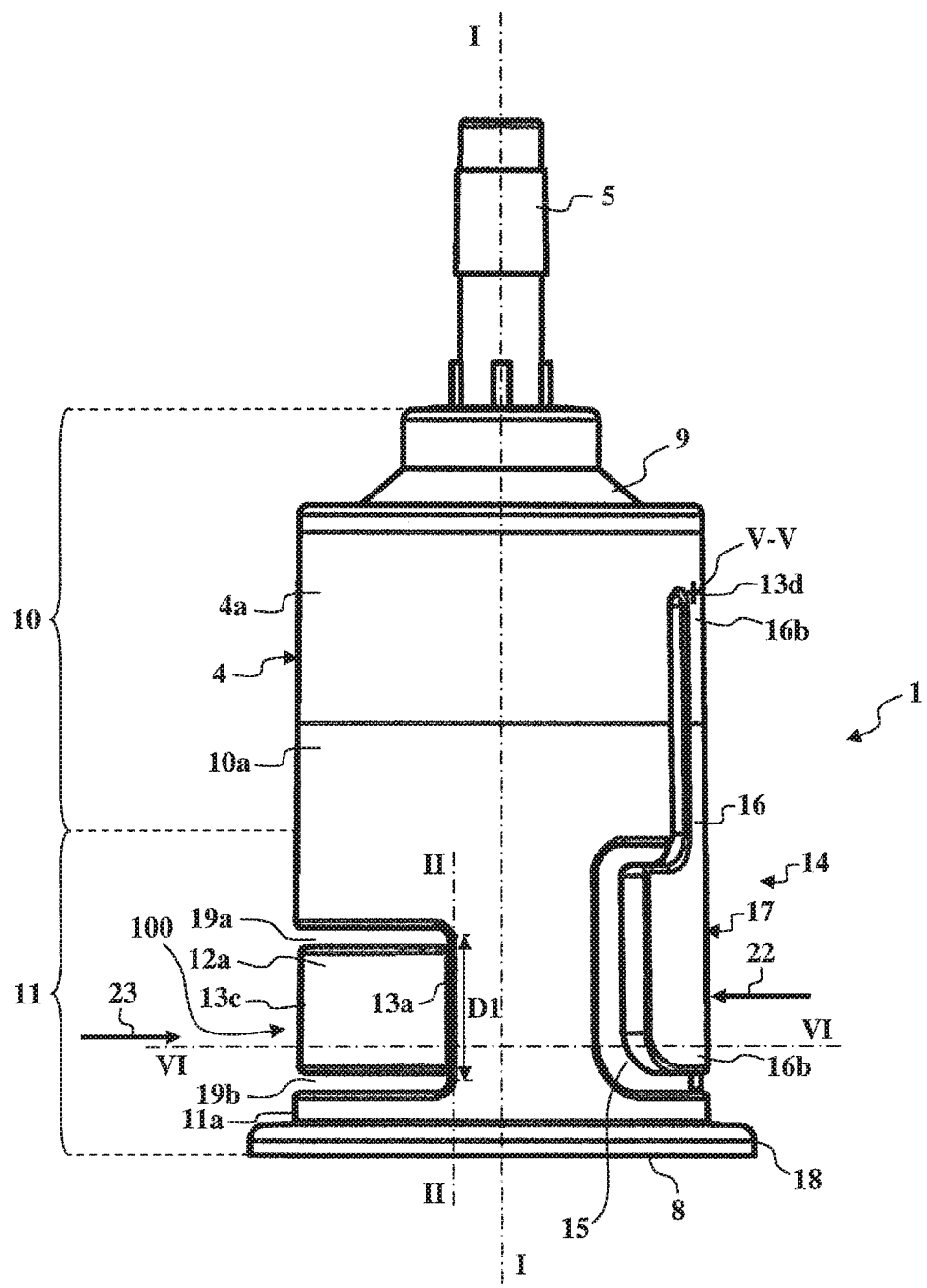
FIG. 1 is a side view of a particular embodiment of a safety connector with needle according to the invention, with first and second flaps in the retracted position.

FIGS. 1 to 7 illustrate a particular embodiment of a safety connector 1 with needle according to the invention. This safety connector 1 with needle comprises a hollow needle 2 for passage of fluid, a needle support sleeve 3, and a tubular protective sleeve 4 extending along a longitudinal axis I-I. The needle support sleeve 3 carries the needle 2, connecting it in a leaktight manner to a fluid-carrying channel 5 to which it is fixed. In this case, the needle support sleeve 3 is formed in one piece with the fluid-carrying channel 5, the assembly formed by the needle support sleeve 3 and by the fluid-carrying channel 5 being overmolded around the needle 2. The tubular protective sleeve 4 is overmolded on the needle support sleeve 3.

The safety connector 1 has a protruding needle portion 6 axially continuing the needle support sleeve 3 at the end opposite the fluid-carrying channel 5. The tubular protective sleeve 4 has an inner space 7 defined by a peripheral sleeve wall 4a and containing the protruding needle portion 6, with an open distal end 8 for the introduction of a sampling container to be connected by the needle 2, and with a proximal end 9 through which the needle support sleeve 3 passes. The tubular protective sleeve 4 has a proximal segment 10 with a proximal peripheral wall 10a developing from the proximal end 9 in line with the protruding needle portion 6. The tubular protective sleeve 4 additionally has a distal segment 11 with a distal peripheral wall 11a continuing the proximal segment 10 between the protruding needle portion 6 and the distal end 8 of the tubular protective sleeve 4. In other words, the peripheral sleeve wall 4a is formed by the union of the proximal 10a and distal 11a peripheral walls.

Figure 2:
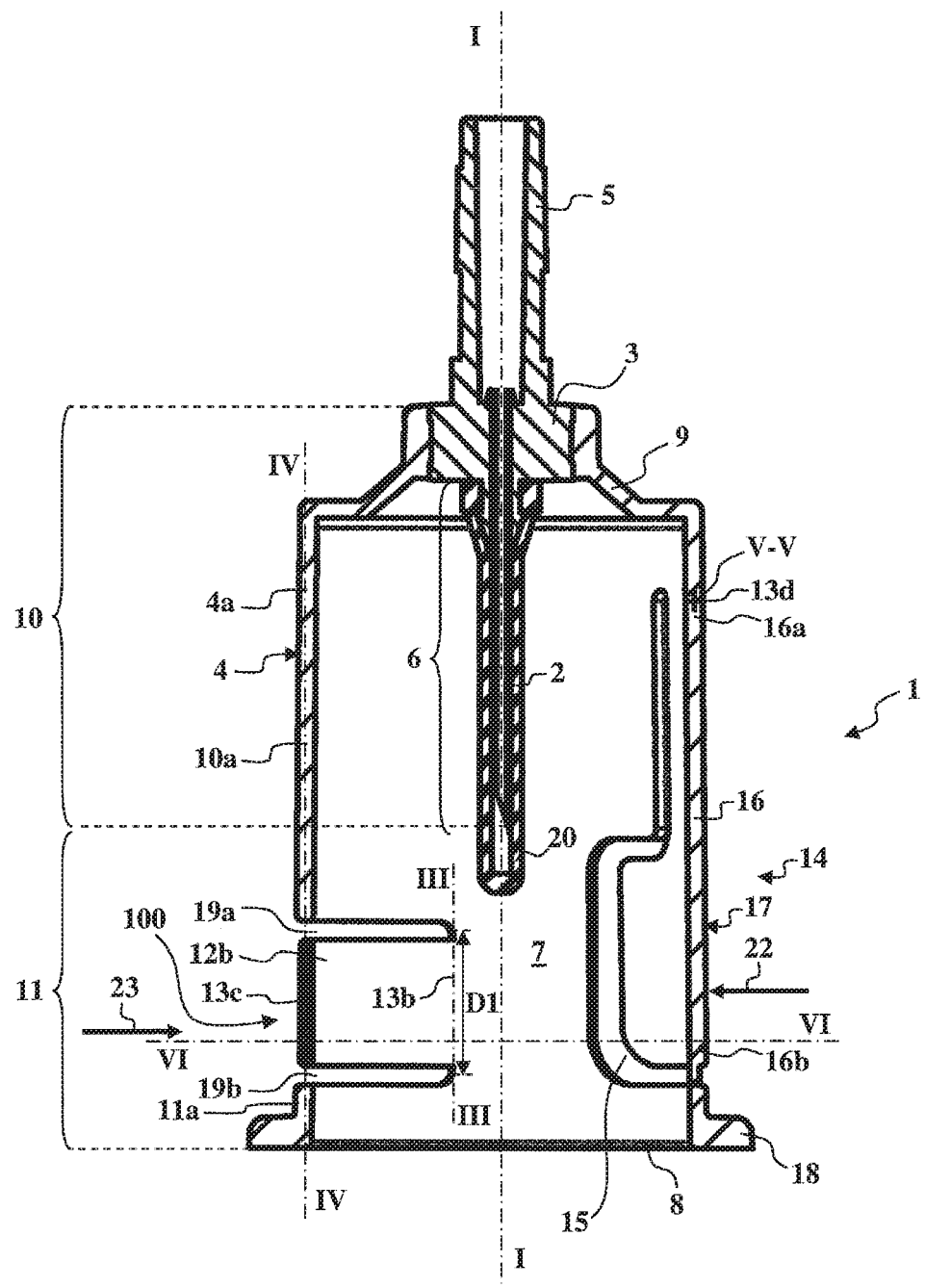
FIG. 2 is a side view, in longitudinal section, of the safety connector with needle from FIG. 1.
Figure 3:
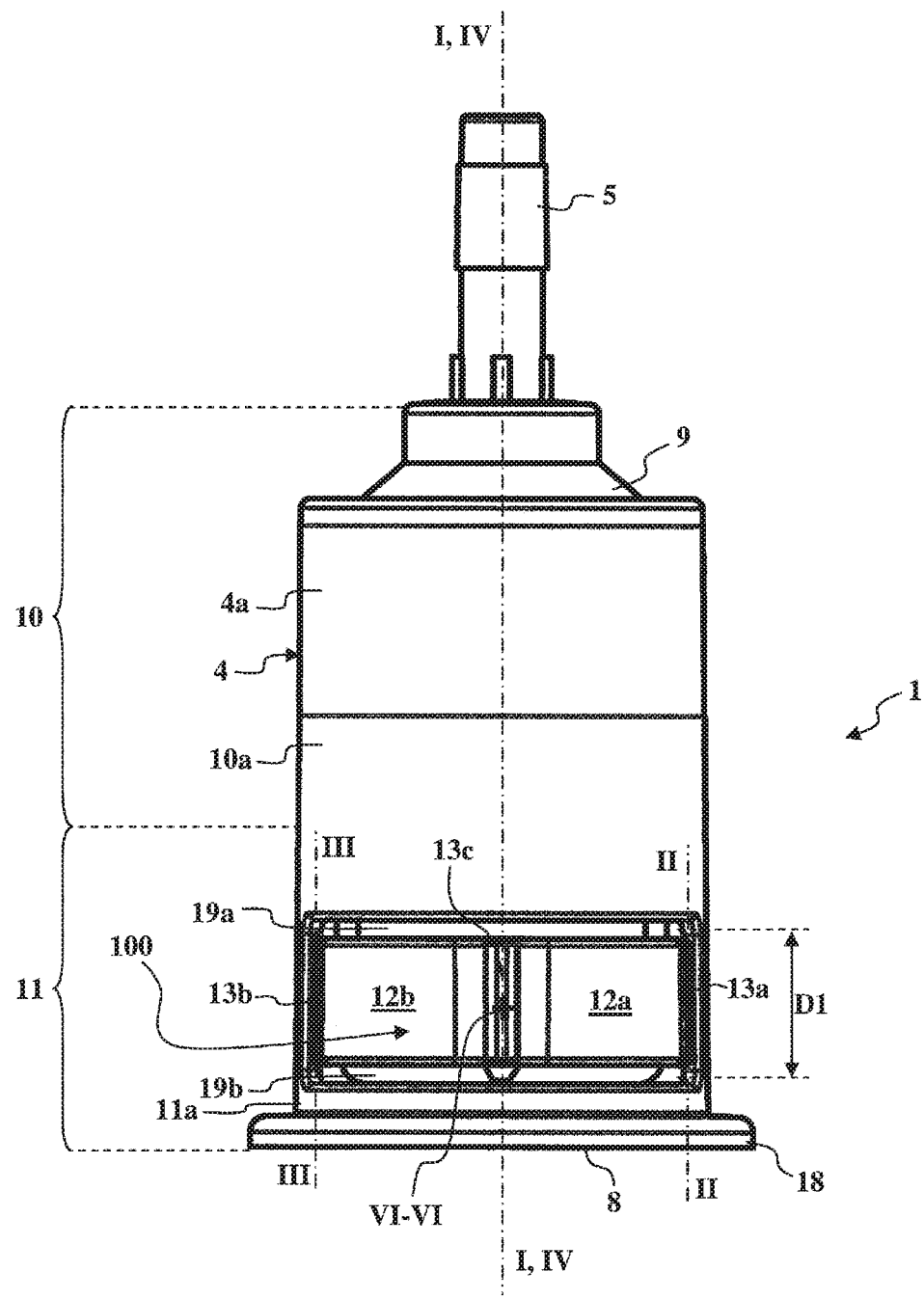
FIG. 3 is a side view of the safety connector with needle from FIG. 1, in a direction perpendicular to the viewing direction of FIG. 1.
Figure 6:
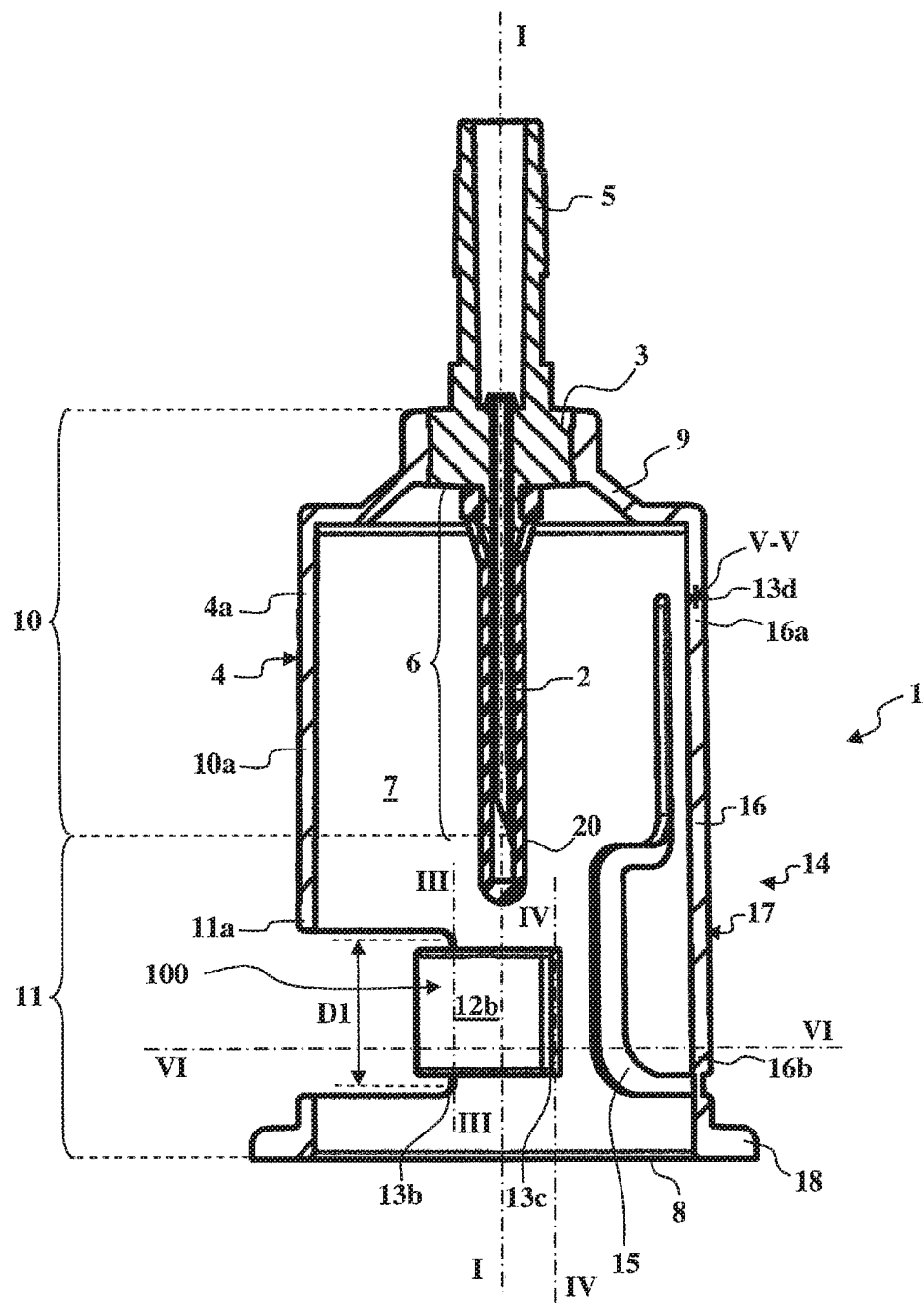
FIG. 6 is a side view, in longitudinal section, of the safety connector with needle from FIG. 1, with the first and second flaps in the projecting position.
Figure 7:
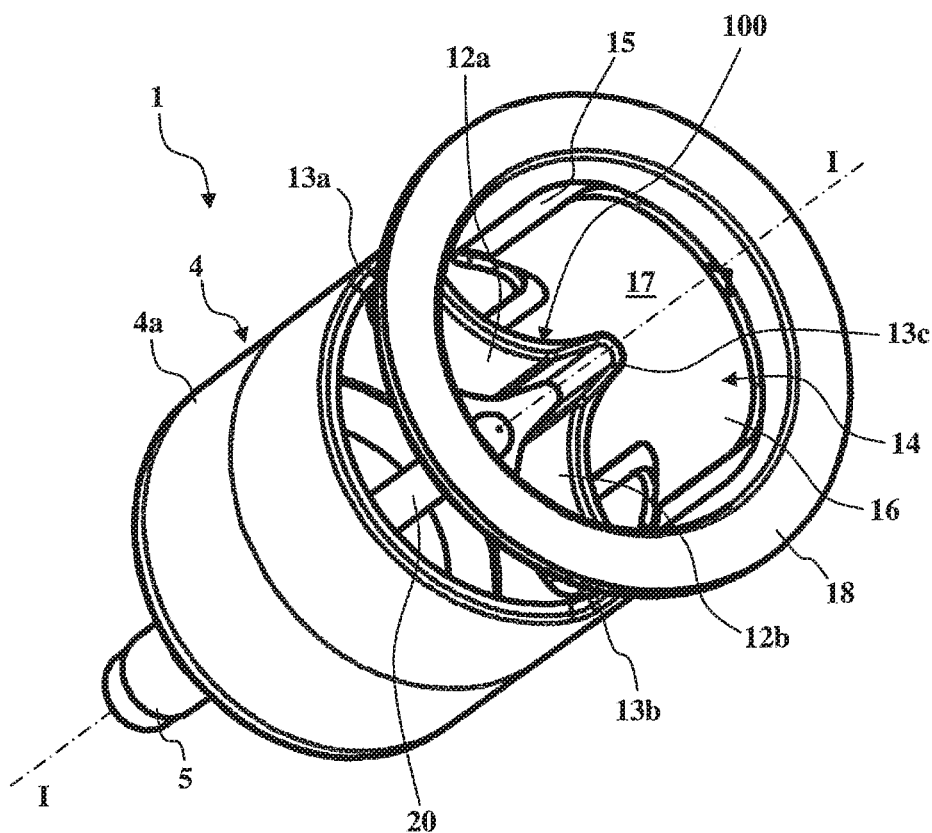
FIG. 7 is a perspective view of the safety connector with needle from FIG. 6.
Figure 8:
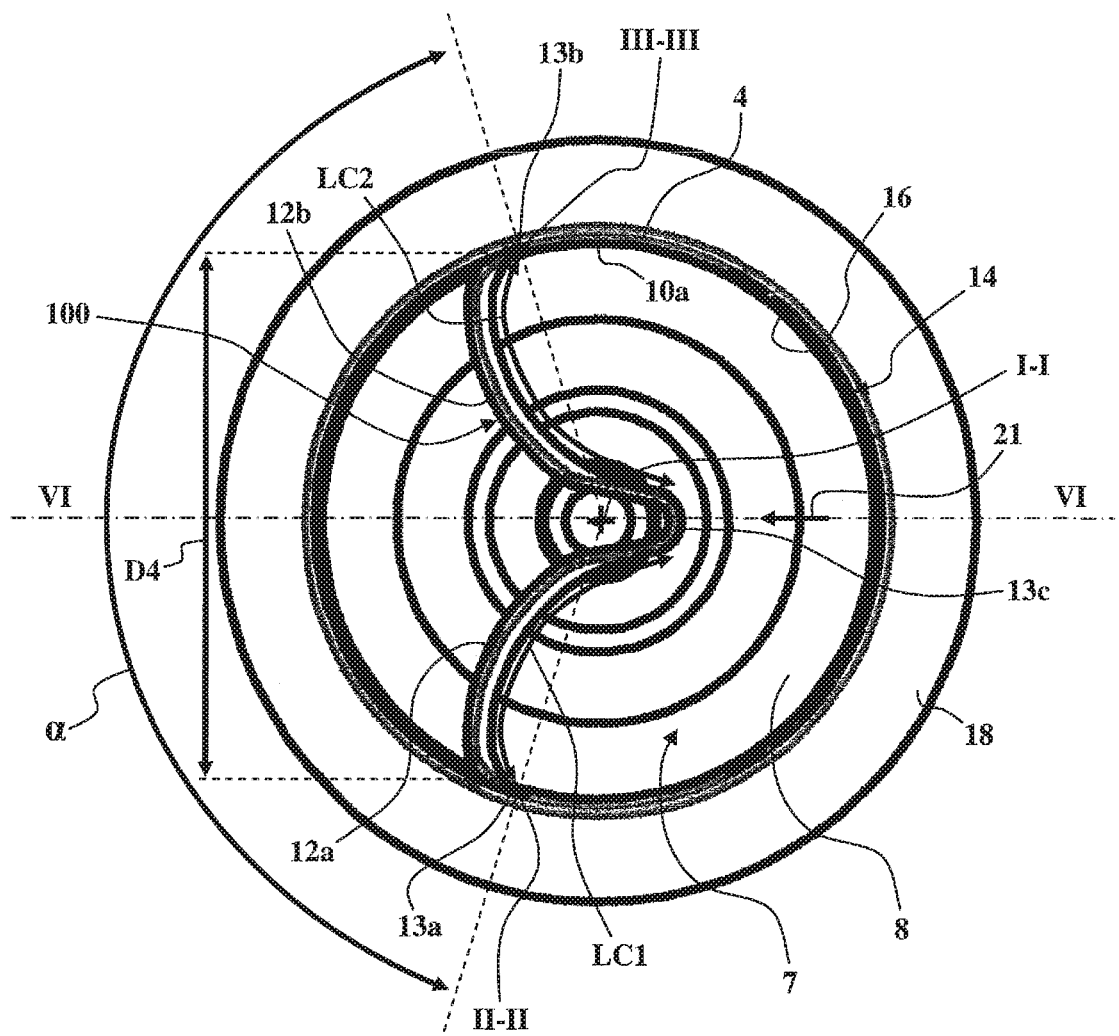
FIG. 8 is a top view of the safety connector with needle from FIG. 6.

It will be seen more particularly from FIG. 3 that the tubular protective sleeve 4 has first and second flaps 12a and 12b formed in the distal peripheral side wall 11a. The flaps 12a and 12b form a movable wall portion 100 which is selectively movable between a retracted position (FIGS. 1 to 5) and a protection position (FIGS. 6 to 8).

In the retracted position, the movable wall portion 100 does not protrude into the inner space 7. In the protection position, the movable wall portion 100 projects into the inner space 7 in order to form an obstacle that at least partially blocks the inner space 7 in the distal segment 11.

The flap 12a is articulated on the rest of the distal peripheral wall 11a at a first hinge zone 13a, while the flap 12b is articulated on the rest of the distal peripheral wall 11a in a second hinge zone 13b. The first hinge zone 13a permits a pivoting of the first flap 12a about a first pivot axis II-II parallel to the longitudinal axis I-I, while the second hinge zone 13b permits a pivoting of the second flap 12b about a second pivot axis III-III parallel to the longitudinal axis I-I.

The first and second flaps 12a and 12b are also articulated on each other in a third hinge zone 13c, permitting a relative pivoting of the first and second flaps 12a and 12b with respect to each other about a third pivot axis IV-IV parallel to the longitudinal axis I-I. The first and second flaps 12a and 12b are thus movable by pivoting about first and second pivot axes II-II and III-III between a retracted position (FIGS. 1 to 5) and a protection position (FIGS. 6 to 8). In the retraced position (FIGS. 1 to 5), the first and second flaps 12a and 12b are aligned with the proximal peripheral wall 10a. In the protection position (FIGS. 6 to 8), the first and second flaps 12a and 12b project into the inner space 7 of the tubular protective sleeve 4.

It will be seen more particularly from FIGS. 6 and 8 that, in the protection position, the flaps 12a and 12b are at least partially situated in the vicinity of the longitudinal axis I-I, as a continuation of the protruding needle portion 6 in the inner space 7 of the tubular protective sleeve 4.

Still in FIG. 8, it will be seen that the tubular protective sleeve 4 has a circular cross section. The first and second pivot axes II-II and III-III are separated from each other by an angle sector α of less than 180°. In this case, the angle sector α is between about 120° and about 170°.

It will be seen from FIG. 3 that the flaps 12a and 12b extend along the longitudinal axis I-I by a distance D1 of between about 12 mm and about 15 mm.

Figure 4:
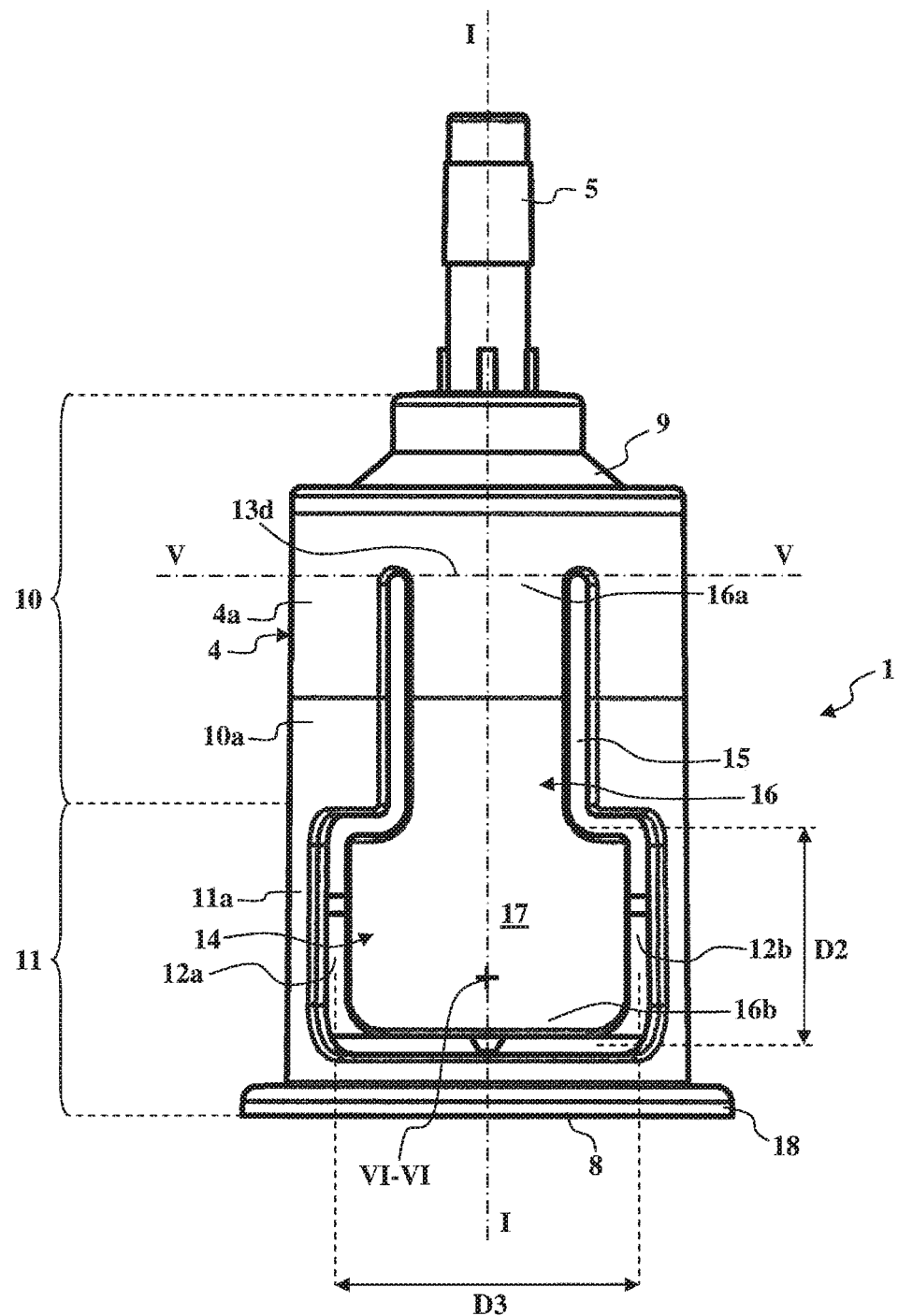
FIG. 4 is a side view of the safety connector with needle from FIG. 1, in a direction perpendicular to the viewing direction of FIG. 1 and counter to the viewing direction of FIG. 3.

It will be seen more particularly from FIG. 4 that the safety connector 1 with needle has pushing means 14, which are formed in the distal peripheral wall 11a and in the proximal peripheral wall 10a by means of a cutout 15. The pushing means 14 are partly situated in line with the flaps 12a and 12b along a transverse axis VI-VI perpendicular to the longitudinal axis I-I. The pushing means 14 are at least partially movable transversely, along the transverse axis VI-VI, between a rest position (FIGS. 2, 4, 5 and 6) and at least one pushing position (FIGS. 9 and 10), and they are returned elastically to their rest position. In the rest position (FIGS. 2, 4, 5 and 6), the pushing means 14 are aligned with the proximal peripheral wall 10a. In the pushing position (FIGS. 9 and 10), the pushing means 14 project into the inner space 7 of the tubular protective sleeve 4 in order to stress the flaps 12a and 12b and return them to the retracted position.

More specifically, the pushing means 14 are in the form of a tongue 16 (FIG. 4) extending along the longitudinal axis I-I between a first end 16a and a free second end 16b. The tongue 16 is articulated at its first end 16a on the rest of the proximal peripheral wall 10a in a fourth hinge zone 13d, permitting a pivoting of the tongue 16 about a fourth pivot axis V-V perpendicular to the longitudinal axis I-I. The free second end 16b of the tongue 16 is situated in line with the flaps 12a and 12b.

In the embodiment illustrated more particularly in FIGS. 2 and 4, the free second end 16b of the tongue 16 has a pushing zone 17 which extends, along the longitudinal axis I-I, by a distance D2 of between about 12 mm and about 15 mm. This pushing zone 17 also extends, perpendicularly with respect to the longitudinal axis I-I, by a distance D3 of between about 10 mm and about 18 mm.

Figure 10:
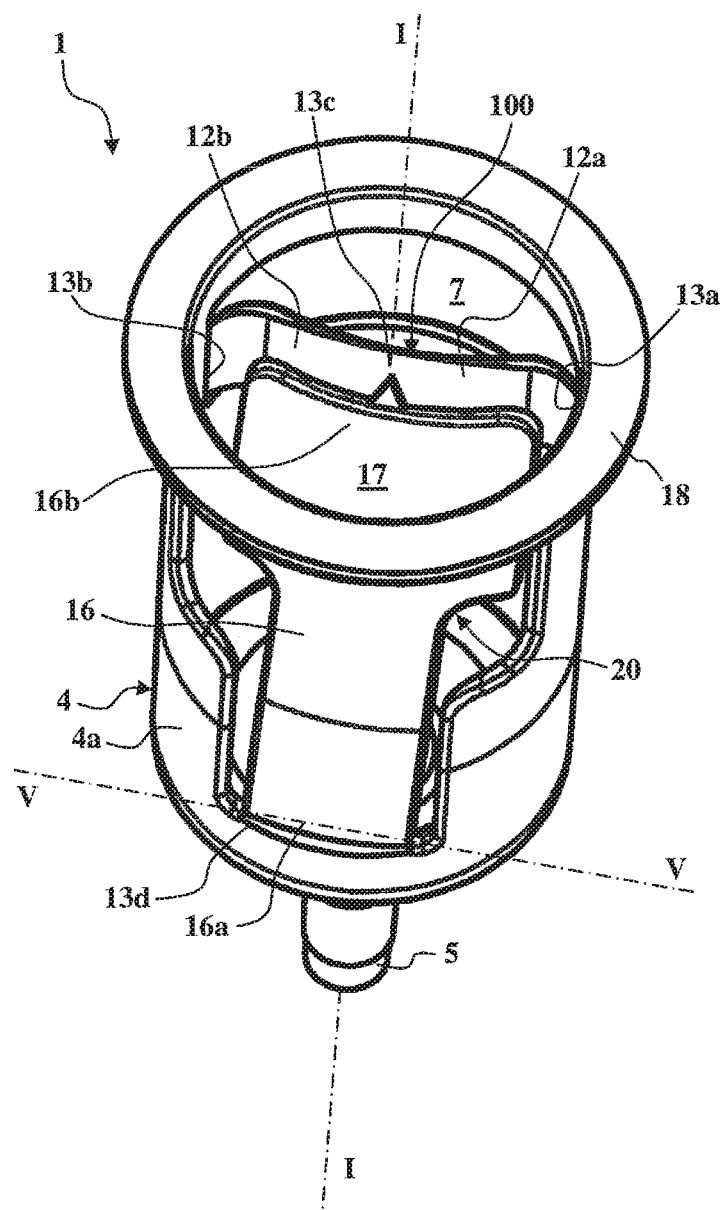
FIG. 10 is a perspective view of the safety connector with needle from FIG. 9.

It will be seen more particularly from FIGS. 2 and 10 that the pushing means 14 are situated diametrically opposite the third hinge zone 13c in relation to the longitudinal axis I-I.

The first, second and third hinge zones 13a to 13c are formed by a local thinning of the material thickness of the peripheral wall 4a of the tubular protective sleeve 4. The tubular protective sleeve 4 is made of plastic.

It will be seen more particularly from FIGS. 1 to 3 that the tubular protective sleeve 4 has a radial widening 18 at its open distal end 8. The first and second flaps 12a and 12b are formed, along the longitudinal axis I-I, in immediate proximity to the open distal end 8. "Immediate proximity" signifies a distance of between 1 mm and 5 mm.

To produce the safety connector 1 with needle as illustrated in FIGS. 1 to 10, it is possible to perform a single plastic injection-molding step during which the tubular protective sleeve 4 is formed in one go and provided with:
cutouts 19a and 19b forming the flaps 12a and 12b,
thinning of the material thickness to form the first, second and third hinge zones 13a to 13c,
cutouts 15 forming the pushing means 14.

In practice, the cutouts 15, 19a and 19b can be made by means of transverse mold cores.

When the tubular protective sleeve 4 of the safety connector 1 with needle is produced by plastic injection molding, it has a clearance angle giving it a slightly frustoconical peripheral side wall 4a.

During its use by an operator, for example for taking a blood sample, the safety connector 1 with needle is supplied with its first and second flaps 12a and 12b in the protection position (FIGS. 6 to 8). In this position, the flaps 12a and 12b, projecting into the inner space 7 of the tubular protective sleeve 4 in the area of the distal segment 11 of the tubular protective sleeve 4, prevent an object or a finger from bearing against the needle 2 when introduced into the tubular protective sleeve 4 via the open distal end 8 thereof. This is because said object, or the operator's finger, then comes to bear, along the longitudinal axis I-I, against the first and second flaps 12a and 12b and cannot penetrate as far as the proximal segment 10 of the tubular protective sleeve 4.

When the first and second flaps 12a and 12b are in the protection position, it will be seen more particularly from FIG. 8 that the distance D4 separating the first and second hinge zones 13a and 13b is less than the sum of the arc lengths LC2 and LC1 of the first and second flaps 12a and 12b. For this reason, the first and second flaps 12a and 12b are situated in a stable position of equilibrium.

When the operator wishes to engage a sampling tune in the inner space 7, he starts by moving the first and second flaps 12a and 12b from their protection position (FIGS. 6 to 8) to their retracted position (FIGS. 1 to 5). This movement can be effected by one of the operator's fingers coming to bear directly against the first and second flaps 12a and 12b and/or against the third hinge zone 13c in order to move the third hinge zone 13c transversely along the transverse axis VI-VI in a movement illustrated by the arrow 21 in FIG. 8.

Figure 9:
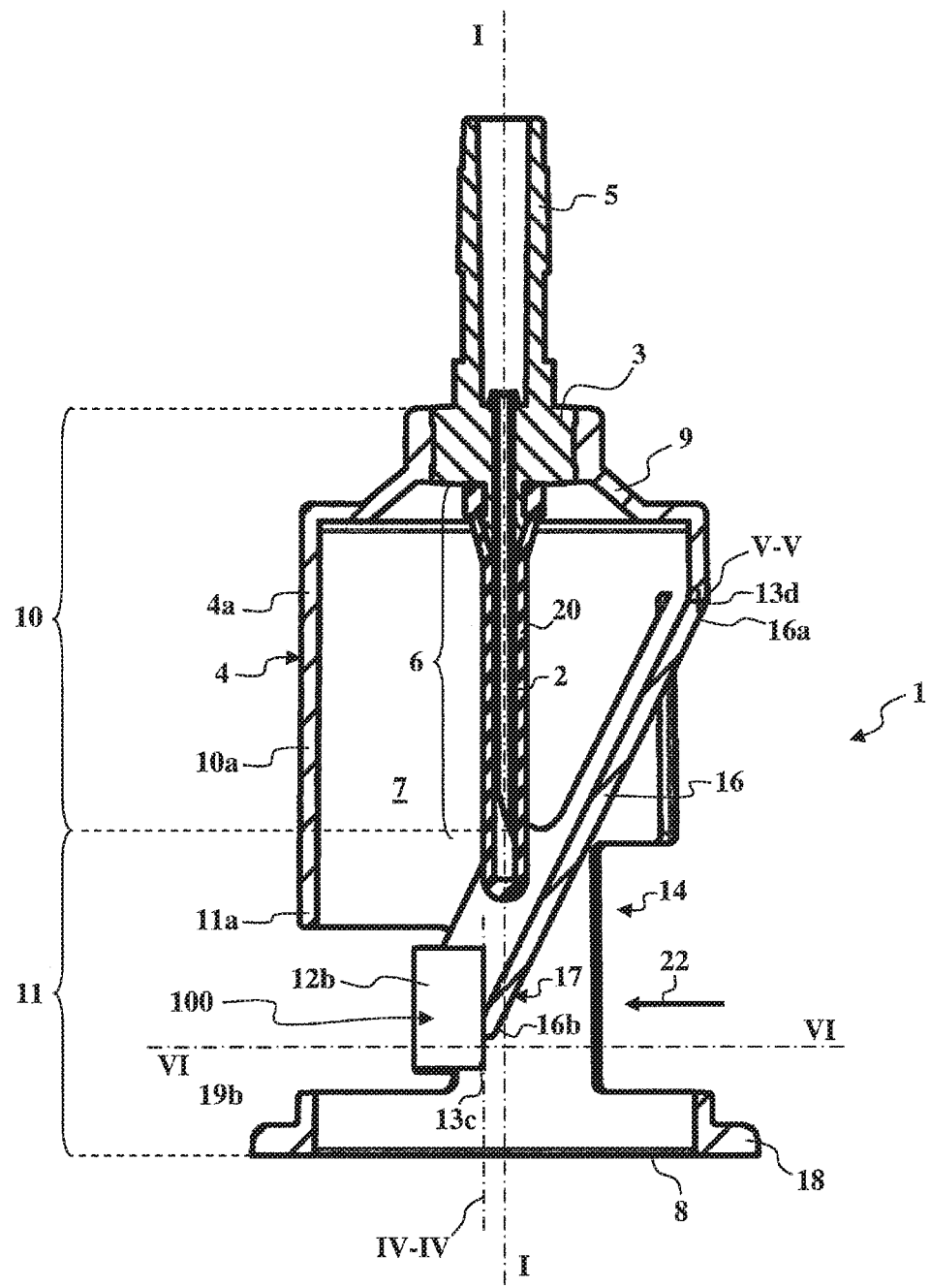
FIG. 9 is a side view, in longitudinal section, of the safety connector with needle from FIG. 1, with pushing means that push the first and second flaps from their projecting position back to their retracted position.

Alternatively, the operator may use the pushing means 14, which effectively limit the risks of one of the operator's fingers coming into contact with the needle 2. In practice, the operator applies a pushing force, illustrated by the arrow 22 in FIG. 2, on the pushing zone 17 of the tongue 16 in such a way as to move this pushing zone 17 transversely along the transverse axis VI-VI in the direction of the third hinge zone 13c. After a certain travel, the pushing zone 17 comes into contact with the third hinge zone 13c and/or the first and second flaps 12a and 12b (FIGS. 9 and 10). By continuing the pushing movement illustrated by the arrow 22 in FIG. 2, the operator pushes the first and second flaps 12a and 12b from their projecting position back to their retracted position (FIGS. 1 to 5).

The retracted position of the first and second flaps 12a and 12b is also a stable position of equilibrium, the sum of the arc lengths LC1 and LC2 of the first and second flaps 12a and 12b being greater than the distance D4 separating the first and second hinge zones 13a and 13b.

During the movement of the first and second flaps 12a and 12b from their protection position to their retracted position, the first and second flaps 12a and 12b deform elastically (adopting a more pronounced curvature) and/or the distal segment 11 of the tubular protective sleeve 4 deforms gently and elastically (adopting an oval shape). Said elastic deformation or deformations allow the first and second flaps 12a and 12b to go from their projecting position to their retracted position (and vice versa) although the sum of the arc lengths LC1 and LC2 is greater than the distance D4 separating the first and second hinge zones 13a and 13b. The deformation capacity of the flaps 12a and 12b and/or of the distal segment 11 of the tubular protective sleeve 4 can be optimized by the choice of suitable plastic (polypropylene copolymer or polyacetal for example), by suitable material thicknesses, and also by providing a suitable distance between the flaps 12a and 12b and the radial widening 18 provided for stiffening.

The retracted position and the protection position are therefore positions of stable equilibrium for the first and second flaps 12a and 12b. In other words, when the first and second flaps 12a and 12b are moved slightly from their retracted position toward their protection position (or conversely from their protection position toward their retracted position), they tend to return to their retracted position (or protection position). It is only beyond a movement of predetermined extent of the first and second flaps 12a and 12b that the latter pass from their retracted position to their protection position (or conversely from their protection position to their retracted position).

Figure 5:
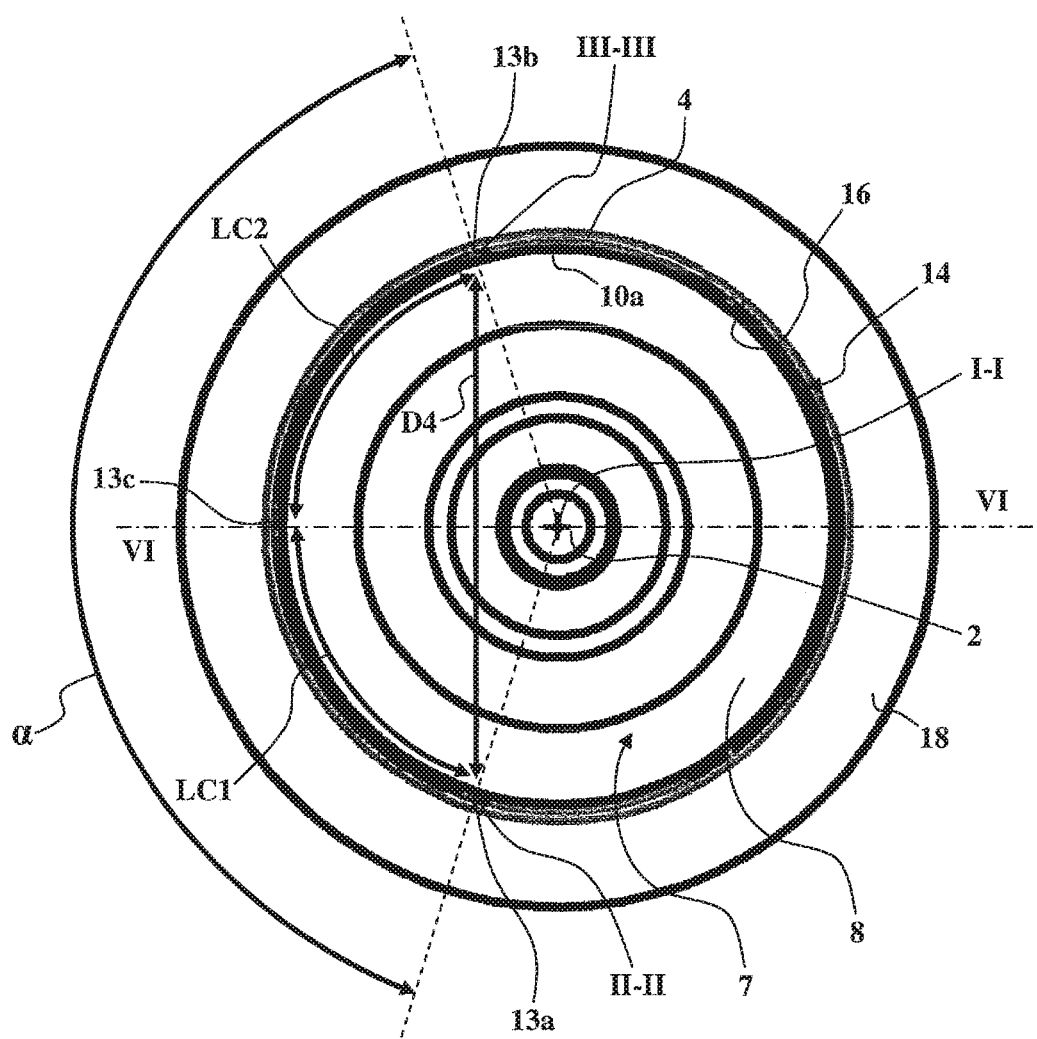
FIG. 5 is a top view of the safety connector with needle from FIG. 1.

Once the first and second flaps 12a and 12b are in the retracted position, they are aligned with the proximal peripheral wall 10a, such that they no longer protrude into the inner space 7 of the tubular protective sleeve 4 (FIG. 5). The inner space 7 is thus available, and remains available or account of the stable equilibrium of the first and second flaps 12a and 12b in the retracted position, to receive a sampling tube engaged by the operator in the tubular protective sleeve 4 via the open distal end 8 of the latter.

After the sampling, the operator withdraws the sampling tube from the tubular protective sleeve 4 and has to discard the safety connector 1, which is for single use only. However, before discarding the safety connector 1 with needle, it is important for the operator to ensure that no one can be accidentally pricked by the needle 2. To do this, the operator applies a radial pushing force, illustrated by the arrow 23 in FIG. 2, to the first and second flaps 12a and 12b in such a way as to move the latter from their retracted position to their protection position. Once the first and second flaps 12a and 12b are in the protection position, the operator may discard the safety connector 1. In the absence of deliberate stress aimed at moving the first and second flaps 12a and 12b to their retracted position, said flaps 12a and 12b remain in the protection position by virtue of their stable equilibrium in the protection position.

The protruding needle portion 6 is enveloped by a perforable protective sheath 20 which is made of elastomer and which, when a sampling tube is to be perforated by the needle 2, rolls up along the needle 2 in the direction of the proximal end 9 of the tubular protective sleeve 4. The protective sheath 20 protrudes into the distal segment 11 but is not situated in line with the flaps 12a and 12b, so as not to impede the movements of the latter.

In the embodiment illustrated in FIGS. 1 to 10, the fluid-carrying channel 5 is preferably intended to be connected to the end of a tube, the other end of the latter being connected to a needle that is intended to penetrate a vein of the patient.

Figure 11:
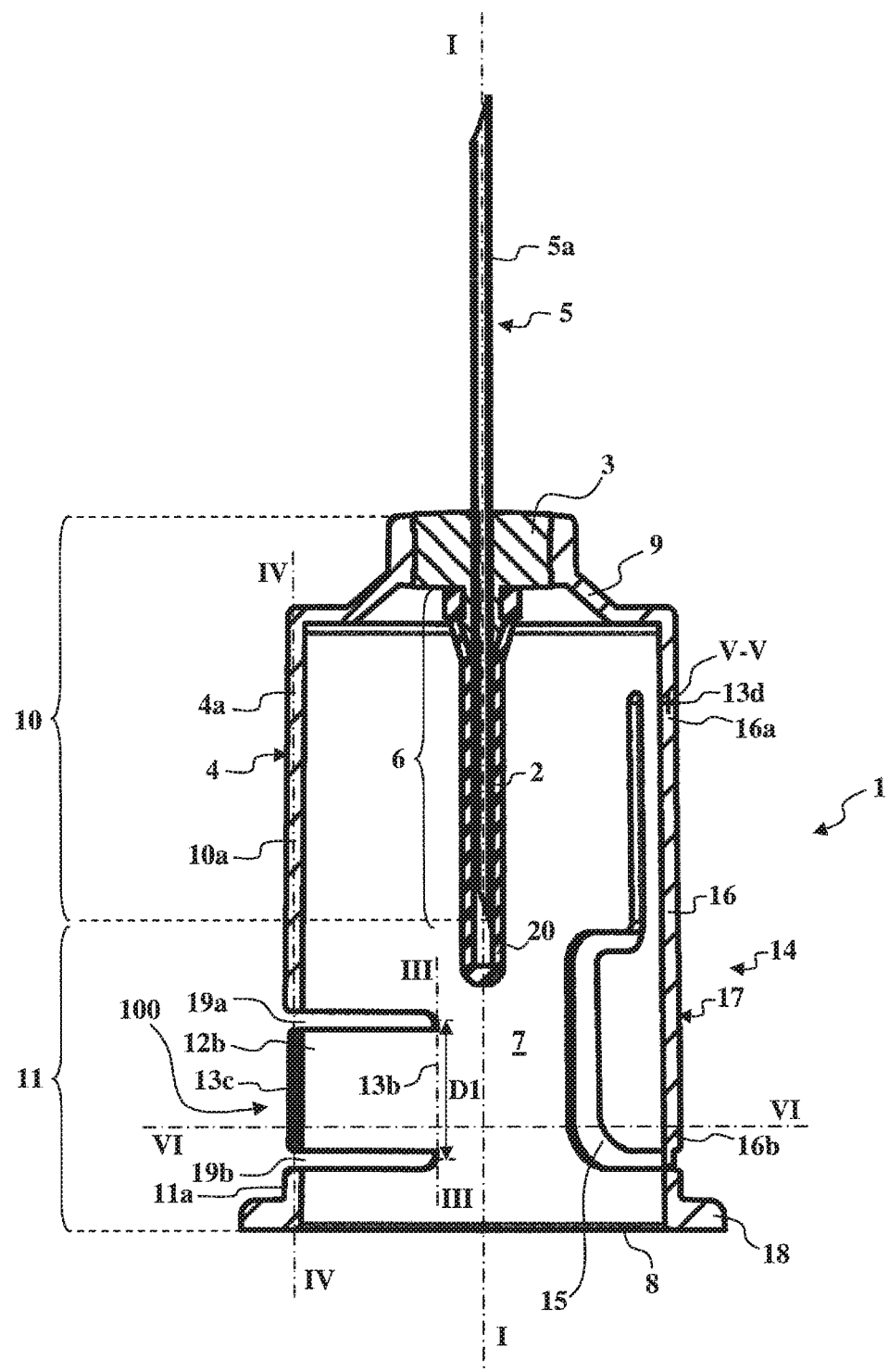
FIG. 11 is a side view, in longitudinal section, of another particular embodiment of a safety connector with needle according to the invention.

Alternatively, as is illustrated in the particular embodiment in FIG. 11, the fluid-carrying channel 5 can comprise a protruding needle portion 5a similar to the protruding needle portion 6. In FIG. 11, the protruding needle portion 5a forms one and the same needle along with the protruding needle portion 6. This is therefore referred to as a double needle 2. The needle support sleeve 3 is overmolded around the double needle 2.

The safety connector 1 can then be used with its protruding needle portion 5a engaged directly in the vein of a patient during a blood sampling procedure.

The present invention is not limited to the embodiments that have been explicitly described and instead includes variants and generalizations thereof within the scope of the appended claims.

The invention claimed is:

1. A safety connector with needle, comprising a hollow needle for passage of fluid, a needle support sleeve, and a tubular protective sleeve extending along a central longitudinal axis (I-I), the needle being connected in a leaktight manner to a fluid-carrying channel to which the needle support sleeve is fixed, a protruding needle portion axially continuing the needle support sleeve at the end opposite the fluid-carrying channel, the tubular protective sleeve having an inner space defined by a peripheral sleeve wall and containing the protruding needle portion, with an open distal end for the introduction of a sampling container to be connected by the needle, and with a proximal end through which the needle support sleeve passes, the tubular protective sleeve having a proximal segment with a proximal peripheral wall developing from its proximal end in line with the protruding needle portion, and having a distal segment with a distal peripheral wall continuing the proximal segment from the protruding needle portion to the distal end of the tubular protective sleeve, wherein:
the distal peripheral wall has at least one wall portion selectively movable between a retracted position and a protection position,
in the retracted position, the movable wall portion does not protrude into the inner space,
in the protection position, the movable wall portion projects into the inner space in order to form an obstacle between a finger of an operator and the protruding needle portion, that at least partially blocks the inner space in the distal segment between the protruding needle portion and the distal end of the tubular protective device.

2. The safety connector with needle as claimed in claim 1, wherein, in the protection position, the movable wall portion is in a continuation of the protruding needle portion in the inner space of the tubular protective sleeve, and wherein the movable wall portion is sufficiently close to the central longitudinal axis (I-I) so as to form an obstacle between a finger of an operator and the protruding needle portion.

3. The safety connector with needle as claimed in claim 1, wherein:

the movable wall portion has first and second flaps formed in the distal peripheral wall, the first and second flaps are respectively articulated on the rest of the distal peripheral wall in a first hinge zone and a second hinge zone, respectively permitting a pivoting of the first and second flaps about a first pivot axis (II-II) and a second pivot axis (III-III) parallel to the longitudinal axis (I-I), the first and second flaps are articulated on each other in a third hinge zone, permitting a relative pivoting of the first and second flaps with respect to each other about a third pivot axis (IV-IV) parallel to the longitudinal axis (I-I), the first and second flaps are movable by pivoting, about first (II-II) and second (III-III) pivot axes, between a retracted position and a protection position, in the retracted position, the first and second flaps are aligned with the proximal peripheral wall, in the protection position, the first and second flaps project into the inner space of the tubular protective sleeve.

4. The safety connector with needle as claimed in claim 3, wherein the first, second and third hinge zones are produced by a local thinning of the material thickness of the peripheral sleeve wall.

5. The safety connector with needle as claimed in claim 3, wherein:

the tubular protective sleeve has a circular cross section, the first (II-II) and second (III-III) pivot axes are separated from each other by an angle sector of less than 180°.

6. The safety connector with needle as claimed in claim 5, wherein the first (II-II) and second (III-III) pivot axes are separated from each other by an angle sector ($\alpha$) of between about 120° and about 170°.

7. The safety connector with needle as claimed in claim 1, wherein the movable wall portion extends, along the longitudinal axis (I-I), by a distance (D1) of between about 12 mm and about 15 mm.

8. The safety connector with needle as claimed in claim 1, wherein:

the safety connector with needle has pushing means which are formed in the distal peripheral wall and/or in the proximal peripheral wall and are situated at least partially in line with the movable wall portion, the pushing means are at least partially movable transversely between a rest position and at least one pushing position, being returned elastically to their rest position, in the rest position, the pushing means do not protrude into the inner space and are preferably aligned with the proximal peripheral wall, in the pushing position, the pushing means project into the inner space of the tubular protective sleeve in order to stress the movable wall portion and return it to the retracted position.

9. The safety connector with needle as claimed in claim 8, wherein:

the pushing means are in the form of a tongue extending along the longitudinal axis (I-I) between a first end and a free second end, the tongue is articulated at its first end on the rest of the proximal peripheral wall and/or of the distal peripheral wall in a fourth hinge zone, permitting a pivoting of the tongue about a fourth pivot axis (V-V) perpendicular to the longitudinal axis (I-I), the free second end of the tongue is situated in line with the movable wall portion.

10. The safety connector with needle as claimed in claim 9, wherein the free second end of the tongue has a pushing zone which extends, along the longitudinal axis (I-I), by a distance (D2) of between about 12 mm and about 15 mm and extends, perpendicularly with respect to the longitudinal axis (I-I), by a distance (D3) of between about 10 mm and about 18 mm.

11. The safety connector with needle as claimed in claim 8, wherein the pushing means are situated diametrically opposite the movable wall portion in relation to the longitudinal axis (I-I).

12. The safety connector with needle as claimed in claim 1, wherein the tubular protective sleeve is made of plastic.

13. The safety connector with needle as claimed in claim 1, wherein:

the tubular protective sleeve has, at its open distal end, a radial widening, the tubular protective sleeve extends along the longitudinal axis (I-I), from the movable wall portion towards the open distal end, the movable wall portion being spaced from the open distal end by a distance of between 1 mm and 5 mm.

14. The safety connector with needle as claimed in claim 1, wherein the tubular protective sleeve is overmolded on the needle support sleeve.

15. A method for producing a safety connector with needle as claimed in claim 1, comprising a step of plastic injection molding, during which the tubular protective sleeve is formed in one go and provided with cutouts forming the movable wall portion.

16. The method of claim 15, further comprising providing the tubular protective sleeve with a reduced material thickness forming the movable wall portion.

17. The method of claim 15, further comprising providing the tubular protective sleeve with cutouts forming the pushing means.

* * * * *